United States Patent
Suzuki et al.

(10) Patent No.: US 11,701,304 B2
(45) Date of Patent: Jul. 18, 2023

(54) DENTAL RESTORATIVE MATERIAL AND RESIN MATERIAL FOR DENTISTRY CUTTING FORMED OF SAME

(71) Applicant: Tokuyama Dental Corporation, Taito-ku (JP)

(72) Inventors: Takuya Suzuki, Tsukuba (JP); Hideki Kazama, Tsuchiura (JP)

(73) Assignee: Tokuyama Dental Corporation, Taito-ku (JP)

( * ) Notice: Subject to any disclaimer, the term of this patent is extended or adjusted under 35 U.S.C. 154(b) by 388 days.

(21) Appl. No.: 16/956,917

(22) PCT Filed: Dec. 26, 2018

(86) PCT No.: PCT/JP2018/047916
§ 371 (c)(1),
(2) Date: Jun. 22, 2020

(87) PCT Pub. No.: WO2019/131788
PCT Pub. Date: Jul. 4, 2019

(65) Prior Publication Data
US 2020/0330333 A1   Oct. 22, 2020

(30) Foreign Application Priority Data

Dec. 26, 2017 (JP) .............................. JP2017-249918
Jun. 1, 2018 (JP) .............................. JP2018-105970

(51) Int. Cl.
| | | |
|---|---|---|
| A61F 2/00 | (2006.01) | |
| A61K 8/72 | (2006.01) | |
| C08G 61/02 | (2006.01) | |
| C08F 2/46 | (2006.01) | |
| C08F 2/50 | (2006.01) | |
| C08G 61/04 | (2006.01) | |
| A61K 6/893 | (2020.01) | |
| A61K 6/62 | (2020.01) | |
| A61K 6/17 | (2020.01) | |
| B29C 39/00 | (2006.01) | |
| B29C 39/02 | (2006.01) | |
| B29C 39/38 | (2006.01) | |
| C08G 18/32 | (2006.01) | |
| C08G 18/34 | (2006.01) | |
| C08G 18/38 | (2006.01) | |
| C08G 18/76 | (2006.01) | |
| B29K 275/00 | (2006.01) | |
| B29K 509/02 | (2006.01) | |

(52) U.S. Cl.
CPC .............. *A61K 6/893* (2020.01); *A61K 6/17* (2020.01); *A61K 6/62* (2020.01); *B29C 39/003* (2013.01); *B29C 39/02* (2013.01); *B29C 39/38* (2013.01); *C08G 18/3206* (2013.01); *C08G 18/341* (2013.01); *C08G 18/348* (2013.01); *C08G 18/3876* (2013.01); *C08G 18/7621* (2013.01); *C08G 18/7642* (2013.01); *B29K 2275/00* (2013.01); *B29K 2509/02* (2013.01)

(58) Field of Classification Search
CPC . A61K 6/893; A61K 6/76; A61K 6/71; A61K 6/17; A61K 6/64; A61K 6/62; A61K 6/887; B29C 39/02; B29C 39/003; B29C 39/38; C08K 9/06; C08K 3/22; C08K 3/36; C08K 2003/2241; C08K 2003/2244; C08K 2003/2227; C08K 2201/003; A61C 13/022; A61C 13/087; C08G 18/341; C08G 18/7621; C08G 18/3876; C08G 18/3206; C08G 18/7642; C08G 18/465; C08G 18/348; C08G 18/675; C08F 39/02; C08F 299/065; C08L 75/04; C08L 75/16; C08L 33/10; B29K 2275/00; B29K 2509/02
USPC ........ 523/115, 113, 105, 1; 522/6, 189, 184, 522/71, 1; 520/1
See application file for complete search history.

(56) References Cited

U.S. PATENT DOCUMENTS

| | | | |
|---|---|---|---|
| 4,089,763 | A | 5/1978 | Dart et al. |
| 4,110,184 | A | 8/1978 | Dart et al. |
| 4,787,850 | A | 11/1988 | Michl et al. |
| 5,378,737 | A | 1/1995 | Jacobs et al. |

(Continued)

FOREIGN PATENT DOCUMENTS

| | | |
|---|---|---|
| JP | 50-42696 | 4/1975 |
| JP | 2002-527588 A | 8/2002 |

(Continued)

OTHER PUBLICATIONS

Ishizaka et al, JP 2012-012333 Machine Translation, Jan. 19, 2012 (Year: 2012).*
Zheng et al, Catalyst-Free thermoset polyurethane with permanent shape reconfigurability and highly tunable triple-shape memory performance, Mar. 15, 2017, ACS Macro Lett. 2017, 6, 326-330 (Year: 2017).*
Extended European Search Report dated Jul. 30, 2021 in corresponding European Patent Application No. 18895595.9, 14 pages.

(Continued)

*Primary Examiner* — Jessica Whiteley
(74) *Attorney, Agent, or Firm* — Oblon, McClelland, Maier & Neustadt, L.L.P.

(57) ABSTRACT

The dental restorative material of the present invention is a dental restorative material that contains a resin matrix and an inorganic filler in an amount of 25 to 1,000 parts by mass per 100 parts by mass of the resin matrix, and in the dental restorative material, the resin matrix contains a polyurethane resin, and the inorganic filler has an average particle diameter of 0.001 to 100 μm. According to the present invention, a dental restorative material that has a high bending strength and a high surface hardness, and is excellent in transparency and cutting workability, and a resin material for dental cutting work containing the same can be provided.

8 Claims, No Drawings

(56) References Cited

U.S. PATENT DOCUMENTS

| | | |
|---|---|---|
| 7,132,459 B1 | 11/2006 | Buchel |
| 2003/0166741 A1 | 9/2003 | Klare et al. |
| 2012/0021383 A1 | 1/2012 | Skaria et al. |
| 2015/0291758 A1* | 10/2015 | Kuwamura ........ C08G 18/6225 521/174 |
| 2015/0374590 A1 | 12/2015 | Chan et al. |

FOREIGN PATENT DOCUMENTS

| | | | |
|---|---|---|---|
| JP | 2007-191598 A | | 8/2007 |
| JP | 2012-12333 A | | 1/2012 |
| JP | 2012012333 | * | 1/2012 |
| JP | 2016-13997 A | | 1/2016 |
| JP | 2017-48121 A | | 3/2017 |
| RU | 2 600 814 C2 | | 10/2016 |

OTHER PUBLICATIONS

Ning Zheng et al., "Catalyst-Free Thermoset Polyurethane with Permanent Shape Reconfigurability and Highly Tunable Triple-Shape Memory Performance", ACS Macro Letters, vol. 6, No. 4, XP055825715, Mar. 15, 2017, pp. 326-330.

Miriam Estevez et al., "Novel Wear Resistant and Low Toxicity Dental Obturation Materials", Materials Letters, vol. 61, No. 14-15, XP022066753, Apr. 29, 2007, pp. 3025-3029.

International Search Report dated Feb. 12, 2019 in PCT/JP2018/047916 filed on Dec. 26, 2018, 2 pages.

Khan et al., "Preparation and characterization of a novel bioactive restorative composite based on covalently coupled polyurethane-nanohydroxyapatite fibres," ELSEVIER, ScienceDirect, Acta Biomaterialia, vol. 4, May 2008, pp. 1275-1287.

Martim et al., "Novel urethane-based polymer for dental applications with decreased monomer leaching," ELSEVIER, Materials Science and Engineering C, vol. 72, Nov. 2016, pp. 192-201.

Combined Russian Office Action and Search Report dated Jan. 27, 2022 in Russian Patent Application No. 2020120972 (with English translation), 22 pages.

* cited by examiner

DENTAL RESTORATIVE MATERIAL AND RESIN MATERIAL FOR DENTISTRY CUTTING FORMED OF SAME

TECHNICAL FIELD

The present invention relates to a dental restorative material that can be favorably applied to a resin material for dental cutting work for producing a dental prosthesis through cutting work, and a resin material for dental cutting work containing the same.

BACKGROUND ART

One of the measures for producing dental prostheses in the dental therapy, such as an inlay, an onlay, a crown, a bridge, and a superstructure of implant, is a method of performing cutting work with a dental CAD/CAM system. The dental CAD/CAM system is a system that designs a dental prosthesis based on three-dimensional coordinate data using a computer, and produces a crown restoration with a cutting machine or the like. The material for cutting work includes various materials, such as glass-ceramics, zirconia, titanium, and a resin. A cured product in a block shape, a disk shape, or the like obtained by curing a curable composition containing an inorganic filler, such as silica, a polymerizable monomer, such as a methacrylate resin, a polymerization initiator, and the like is available as a resin material for dental cutting work. The resin material for dental cutting work receives increasing attention from the standpoint of the high workability, the esthetics, and the strength.

The resin material for dental cutting work is applied to a coronal portion, and is required to have a higher strength in the case of using as a molar tooth or a bridge. However, the currently available resin material for dental cutting work is based on a (meth)acrylic resin and has a limitation in strength. For example, PTL 1 describes a resin material for dental cutting work containing 15 to 70 parts by weight of a (meth)acrylic polymerizable monomer, 30 to 85 parts by weight of silica fillers of 0.9 µm and 5 to 7 µm, a catalyst, and the like, but the bending strength thereof is insufficient. PTL 2 describes a dental composition containing a polyamide used as a mill blank. However, the polyamide is opaque and thus has insufficient esthetics for use in the dental therapy. Furthermore, there is a problem in cutting workability.

It has been known that a polyurethane resin generally has a high strength. For example, PTL 3 describes a polyurethane resin containing an isocyanate having a norbornane skeleton and a polyol or a polythiol having two or more hydroxy groups or thiol groups in one molecule.

PTLs 4 and 5 describe the application of a polyurethane resin to a dental material.

CITATION LIST

Patent Literatures
PTL 1: JP 2016-13997 A
PTL 2: JP 2017-48121 A
PTL 3: JP 2007-191598 A
PTL 4: U.S. Pat. No. 4,787,850
PTL 5: JP 2002-527588 A

SUMMARY OF INVENTION

Technical Problem

The resin material for dental cutting work is demanded to have a high strength, a surface hardness that withstands abrasion in the oral cavity, a high transparency, and good cutting workability. According to the investigations by the present inventors, however, it has been found that the ordinary techniques described above are difficult to provide a material having all the properties.

In view of the background, an object of the present invention is to provide a dental restorative material that has a high strength and a high surface hardness, and is excellent in transparency and cutting workability, and a resin material for dental cutting work containing the same.

Solution to Problem

As a result of the various investigations by the present inventors, it has been found that the problem can be solved by mixing a particular amount of an inorganic filler to a polyurethane matrix.

Accordingly, the present invention provides the following items [1] to [18].

[1] A dental restorative material containing a resin matrix and an inorganic filler in an amount of 25 to 1,000 parts by mass per 100 parts by mass of the resin matrix, the resin matrix containing a polyurethane resin, the inorganic filler having an average particle diameter of 0.001 to 100 µm.

[2] The dental restorative material according to the item [1], wherein the polyurethane resin satisfies the following conditions I and II simultaneously:

$BS_A \geq 200$ (MPa)            condition I $1 \geq BS_W/BS_A \geq 0.70$            condition II wherein $BS_A$ represents a three-point bending strength (unit: MPa) according to ISO 6872, and $BS_W$ represents a three-point bending strength after water immersion (unit: MPa) according to JDMAS 245:2017.

[3] The dental restorative material according to the item [1] or [2], wherein the polyurethane resin is a cured product of a polyurethane raw material polymerizable composition, and the polyurethane raw material polymerizable composition contains:

(A) a polyfunctional isocyanate compound and (B) a polyol compound having at least two hydroxy groups in a molecule or a polythiol compound having at least two thiol groups in a molecule, the polyol compound or the polythiol compound having a distance between the most remote two hydroxy groups or thiol groups in terms of a number of atoms constituting a main chain of a divalent organic residual group intervening between the two hydroxy groups or thiol groups of 2 to 8 in the case where the organic residual group has no ring structure in the main chain, or 3 to 20 in the case where the organic residual group has a ring structure in the main chain provided that all atoms constituting a ring of the ring structure are included in the atoms constituting the main chain, and does not contain a urethane polymerization catalyst.

[4] The dental restorative material according to the item [3], wherein the polyol compound or the polythiol compound (B) has compatibility with the polyfunctional isocyanate compound (A).

[5] The dental restorative material according to the item [3] or [4], wherein the polyol compound or the polythiol compound (B) contains a polyol compound or a polythiol compound having a radical polymerizable group in a molecule.

[6] The dental restorative material according to any one of the items [3] to [5], wherein the polyurethane raw material polymerizable composition further contains (C) a radical polymerizable monomer having a radical polymerizable group (except for a polyol compound and a polythiol compound each having a radical polymerizable group in a molecule).

[7] The dental restorative material according to any one of the items [3] to [6], wherein the polyurethane raw material polymerizable composition further contains (D) a polymerization initiator for the radical polymerizable group.

[8] The dental restorative material according to any one of the items [1] to [7], wherein the inorganic filler is at least one kind selected from the group consisting of silica, alumina, titania, zirconia, and a composite thereof.

[9] A resin material for dental cutting work containing the dental restorative material according to any one of the items [1] to [8].

[10] A polyurethane raw material polymerizable composition containing (A) a polyfunctional isocyanate compound and (B) a polyol compound having at least two hydroxy groups in a molecule or a polythiol compound having at least two thiol groups in a molecule, the polyol compound or the polythiol compound having a distance between the most remote two hydroxy groups or thiol groups in terms of a number of atoms constituting a main chain of a divalent organic residual group intervening between the two hydroxy groups or thiol groups of 2 to 8 in the case where the organic residual group has no ring structure in the main chain, or 3 to 20 in the case where the organic residual group has a ring structure in the main chain provided that all atoms constituting a ring of the ring structure are included in the atoms constituting the main chain, and not containing a urethane polymerization catalyst.

[11] The polyurethane raw material polymerizable composition according to the item [10], wherein the polyol compound or the polythiol compound (B) has compatibility with the polyfunctional isocyanate compound (A).

[12] The polyurethane raw material polymerizable composition according to the item [10] or [11], wherein the polyol compound or the polythiol compound (B) contains a polyol compound or a polythiol compound having a radical polymerizable group in a molecule.

[13] The polyurethane raw material polymerizable composition according to any one of the items [10] to [12], wherein the polyurethane raw material polymerizable composition further contains (C) a radical polymerizable monomer having a radical polymerizable group (except for a polyol compound and a polythiol compound each having a radical polymerizable group in a molecule).

[14] The polyurethane raw material polymerizable composition according to any one of the items [10] to [13], wherein the polyurethane raw material polymerizable composition further contains (D) a polymerization initiator for the radical polymerizable group.

[15] A dental polymerizable composition containing the polyurethane raw material polymerizable composition according to any one of the items [10] to [14] and an inorganic filler.

[16] A method for producing a dental restorative material, including: casting the dental polymerizable composition according to the item [15]; and then curing the composition through a single heating step.

[17] The method for producing a dental restorative material according to the item [16], wherein the dental polymerizable composition is cured through formation of a urethane bond, and radical polymerization of the radical polymerizable group in the heating step.

[18] The method for producing a dental restorative material according to the item [16] or [17], wherein the dental polymerizable composition is prepared by mixing a composition (a) containing the polyfunctional isocyanate compound and a composition (b) containing the polyol compound or the polythiol compound, and at least one of the composition (a) and the composition (b) contains an inorganic filler.

Advantageous Effects of Invention

According to the present invention, a dental restorative material that has a high bending strength and a high surface hardness, and is excellent in transparency and cutting workability, and a resin material for dental cutting work containing the same can be provided.

DESCRIPTION OF EMBODIMENTS

[Dental Restorative Material]

The dental restorative material of the present invention is a dental restorative material that contains a resin matrix and an inorganic filler in an amount of 25 to 1,000 parts by mass per 100 parts by mass of the resin matrix, and in the dental restorative material, the resin matrix contains a polyurethane resin, and the inorganic filler has an average particle diameter of 0.001 to 100 μm.

<Resin Matrix>

The polyurethane resin contained in the resin matrix is not particularly limited, and the polyurethane resin capable of being used in the dental restorative material of the present invention includes not only a polymer having a urethane structure represented by the following (1-1), but also a polymer having a thiourethane structure represented by the following (1-2).

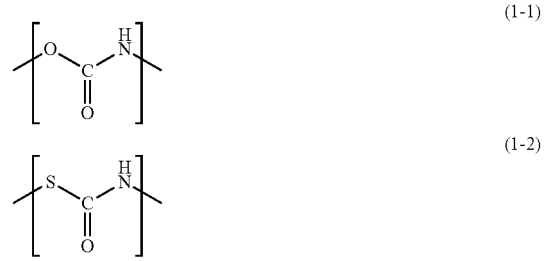

The polyurethane resin capable of being used in the dental restorative material of the present invention is formed through polyaddition, and may be formed through polyaddition of a polyfunctional isocyanate compound and a polyol compound, polyaddition of a polyfunctional isocyanate compound and a polythiol compound, polyaddition of a polyfunctional isocyanate compound, and a polyol compound and a polythiol compound, and the like.

A compound having two or more isocyanate groups in one molecule may be used as the polyfunctional isocyanate without limitation. A compound having two or more hydroxy groups in a molecule may be used as the polyol compound without limitation, and a compound having two or more thiol groups in a molecule may be used as the polythiol compound without limitation.

In the present invention, the polyurethane resin preferably satisfies the following conditions I and II simultaneously:

$BS_A \geq 200$ (MPa)  condition I $1 \geq BS_W/BS_A \geq 0.70$  condition II wherein $BS_A$ represents a three-point bending strength (unit: MPa) according to ISO 6872, and $BS_W$ represents a three-point bending strength after water immersion (unit: MPa) according to JDMAS 245:2017.

The polyurethane resin that satisfies the conditions I and II simultaneously has good water resistance. Accordingly, the dental restorative material that contains the polyurethane resin also has good water resistance and retains a high strength in the oral cavity.

The upper limit of $BS_A$ in the condition I is not particularly limited, and is generally 500 (MPa). The polyurethane resin used in the dental restorative material of the present invention preferably satisfies the following conditions $I_1$ and $II_1$ simultaneously, and more preferably satisfies the following conditions $I_2$ and $II_2$ simultaneously, from the standpoint of the enhancement of the water resistance of the polyurethane resin, the easiness of the production thereof, the easiness of the working thereof, and the like.

$$400 \text{ (MPa)} \geq BS_A \geq 220 \text{ (MPa)} \quad \text{condition } I_1$$

$$1 > BS_W/BS_A \geq 0.75 \quad \text{condition } II_1$$

$$350 \text{ (MPa)} \geq BS_A \geq 250 \text{ (MPa)} \quad \text{condition } I_2$$

$$1 > BS_W/BS_A \geq 0.80 \quad \text{condition } II_2$$

The three-point bending strength $BS_A$ according to ISO 6872 herein is a bending strength obtained by performing a bending test for a specimen in a dry state, and is specifically a value that is determined in the following manner. A polyurethane resin is cut out with a cutting machine or the like and processed with #2000 abrasive paper into a test piece having a width of 4.0 mm±0.2 mm, a thickness of 1.2±0.2 mm, and a length of 14.0 mm or longer. 10 pieces of the test pieces prepared each are measured for the width and the thickness with an accuracy of 0.01 mm and measured with a universal tester (Autograph) under condition of a crosshead speed of 1.0±0.3 mm/min and a supporting point span of 12.0 mm. By using the resulting bending load at the maximum point, the bending strength BS is calculated according to the following expression (1). The 10 test pieces are measured in this manner and the average value of the resulting bending strengths is designated as $BS_A$.

$$BS = 3PS/2WB^2 \quad (1)$$

In the expression, P represents the bending load at the maximum point (N), S represents the supporting point span (12 mm), W represents the width of the test piece (mm), and B represents the thickness of the test piece (mm).

The three-point bending strength after water immersion $BS_W$ according to JDMAS 245:2017 is a bending strength obtained by a bending test after exposing the specimen to water at 37° C. for one week, and is specifically a value that is determined in the following manner. A polyurethane resin is cut out with a cutting machine or the like and processed with #2000 abrasive paper into a test piece having a width of 4.0 mm±0.2 mm, a thickness of 1.2±0.2 mm, and a length of 14.0 mm or longer. 10 pieces of the test pieces prepared are immersed in ion exchanged water while preventing the test pieces from being in contact with each other, and stored at 37° C. for one week. The test pieces are taken out from water, and each are measured for the width and the thickness with an accuracy of 0.01 mm and measured with a universal tester (Autograph) under condition of a crosshead speed of 1.0±0.3 mm/min and a supporting point span of 12.0 mm. By using the resulting bending load at the maximum point, the bending strength BS is calculated according to the expression (1) as similar to the above, and the average value of the 10 test pieces is designated as $BS_W$.

The measurements of $BS_A$ and $BS_W$ are generally applied to a polyurethane resin used in the production of the dental restorative material of the present invention obtained by curing a polymerization curable composition (which may be hereinafter referred to as a "polyurethane raw material polymerizable composition") having the same composition as the polymerization curable composition as the raw material for the production of the polyurethane resin (i.e., the polymerization curable composition excluding the components that do not become the polyurethane resin itself, such as a filler). Specifically, the measurements of $BS_A$ and $BS_W$ are preferably applied to a polyurethane resin obtained by curing a polyurethane raw material polymerizable composition that contains the polyfunctional isocyanate compound and the polyol compound or the polythiol compound used in the production of the dental restorative material of the present invention as the essential components, and further contains the radical polymerizable monomer having a radical polymerizable group added depending on necessity and/or the polymerization initiator having activity to polymerization with the radical polymerizable group added depending on necessity, in which the amount ratios of the components are the same as in the production of the dental restorative material of the present invention. The details of the components are described later.

(Polyurethane Raw Material Polymerizable Composition)

In the dental restorative material of the present invention, the polyurethane resin is preferably a cured product of a polyurethane raw material polymerizable composition that contains the component (A) and the component (B) below and does not contain a urethane polymerization catalyst, from the standpoint of the easiness of the synthesis and the conditions I and II to be definitely satisfied.

Component (A): a polyfunctional isocyanate compound

Component (B): a polyol compound having at least two hydroxy groups in a molecule or a polythiol compound having at least two thiol groups in a molecule, the polyol compound or the polythiol compound having a distance between the most remote two hydroxy groups or thiol groups in terms of a number of atoms constituting a main chain of a divalent organic residual group intervening between the two hydroxy groups or thiol groups of 2 to 8 in the case where the organic residual group has no ring structure in the main chain, or 3 to 20 in the case where the organic residual group has a ring structure in the main chain provided that all atoms constituting a ring of the ring structure are included in the atoms constituting the main chain <Component (A): Polyfunctional Isocyanate Compound>

In the present invention, the polyfunctional isocyanate compound as the component (A) is a compound having two or more isocyanate groups in one molecule, and the polyfunctional isocyanate compound is not particularly limited, as far as the compound has two or more isocyanate groups in one molecule, and be an arbitrary combination of known ones. Specific examples of the polyfunctional isocyanate compound include the following compounds.

(A1) Bifunctional Isocyanate Compound

Examples thereof include 1,3-bis(2-isocyanato-2-propyl)benzene, 2,2-bis(4-isocyanatophenyl)hexafluoropropane, 1,3-bis(isocyanatomethyl)cyclohexane, methylenediphenyl 4,4'-diisocyanate, 3,3'-dichloro-4,4' diisocyanatobiphenyl, 4,4'-diisocyanato-3,3'-dimethylbiphenyl, dicyclohexylmethane 4,4'-diisocyanate, pentamethylene diisocyanate, hexamethylene diisocyanate, norbornane diisocyanate, isophorone diisocyanate, 1,5-diisocyanatonaphthalene, 1,3-phenylene diisocyanate, trimethylhexamethylene diisocyanate, tolylene 2,4-diisocyanate, tolylene 2,6-diisocyanate, and m-xylylene diisocyanate.

(A2) Trifunctional or Higher Functional Isocyanate Compound

Examples thereof include lysine triisocyanate, 4,4',4"-methylidynetris(isocyanatobenzene), and polymethylene polyphenyl polyisocyanate.

These isocyanate compounds may be used alone or as a combination thereof.

<Component (B): Polyol Compound or Polythiol Compound>

The polyol compound or the polythiol compound as the component (B) can be elucidated as follows.

Component (B): a polyol compound satisfying the following conditions (1) and (2) or a polythiol compound satisfying the following conditions (1') and (2').

Condition (1): The polyol compound has at least two hydroxy groups in a molecule.

Condition (2): The polyol compound has a distance between the most remote two hydroxy groups in terms of a number of atoms constituting a main chain of a divalent organic residual group intervening between the two hydroxy groups of 2 to 8 in the case where the organic residual group has no ring structure in the main chain, or 3 to 20 in the case where the organic residual group has a ring structure in the main chain provided that all atoms constituting a ring of the ring structure are included in the atoms constituting the main chain.

Condition (1'): The polythiol compound has at least two thiol groups in a molecule.

Condition (2'): The polythiol compound has a distance between the most remote two thiol groups in terms of a number of atoms constituting a main chain of a divalent organic residual group intervening between the two thiol groups of 2 to 8 in the case where the organic residual group has no ring structure in the main chain, or 3 to 20 in the case where the organic residual group has a ring structure in the main chain provided that all atoms constituting a ring of the ring structure are included in the atoms constituting the main chain.

In the description herein, the distance between the most remote two hydroxy groups in the polyol compound and the distance between the most remote two thiol groups in the polythiol compound, in terms of the number of atoms constituting the main chain, each may be referred to as a number of main chain constituting atoms.

The condition (1) or (1') is the essential condition for forming a polyurethane resin containing the component units bonded via a urethane bond or a thiourethane bond through polyaddition reaction with the component (A). The number of hydroxy groups or thiol groups contained in a molecule is preferably 2 to 6 from the standpoint that the polyurethane resin formed has a sufficient molecular weight and exhibits physical crosslinking and/or chemical crosslinking in a high density, and the standpoint that the hydroxy groups or the thiol groups that may remain in the polyurethane resin can be decreased. In the case where the number of hydroxy groups or thiol groups is too large, there is a tendency that the viscosity is increased in the process of reaction, and hydroxy groups or thiol groups remain to lower the water resistance. The number of hydroxy groups or thiol groups of the polyol compound or the polythiol compound is particularly preferably 2 to 4.

With the condition (2) or (2') satisfied, a crosslinked structure that does not largely adversely affect the transparency and the toughness of the cured product (polyurethane resin) can be introduced to the interior in a relatively high density. The strength and the water resistance of the dental restorative material can be enhanced thereby. In the case where the distance (i.e., the number of main chain constituting atoms) is 1 in the case where the organic residual group has no ring structure in the main chain, the reaction with another isocyanate compound may be impaired through the bulkiness of the urethane bond or the thiourethane bond after the formation thereof through the polyaddition, and consequently the formation of the urethane bond or the thiourethane bond may be impaired. In the case where the distance (i.e., the number of main chain constituting atoms) exceeds 8, the crosslinking density in the cured product may be decreased to lower the water resistance. The distance (i.e., the number of main chain constituting atoms) in this case is preferably 2 to 6, and more preferably 2 to 4.

The distance (i.e., the number of main chain constituting atoms) in the case where the organic residual group has a ring structure in the main chain is necessarily 3 or more, and in the case where the distance exceeds 20 as the upper limit, the crosslinking density in the cured product may be decreased to lower the water resistance, as similar to the above. In the case where the divalent organic residual group intervening between the two hydroxy groups or thiol groups has an aromatic ring and/or alicyclic ring structure, the water resistance can be achieved even in the case where the number of atoms constituting the main chain is larger than the case where the organic residual group has no ring structure in the main chain, due to the interaction derived from the aromatic ring and/or alicyclic ring structure. The distance (i.e., the number of main chain constituting atoms) in this case is preferably 3 to 15, and more preferably 3 to 10.

The polyol compound may be used alone or as a combination of two or more different compounds. Similarly, the polythiol compound may be used alone or as a combination of two or more different compounds. The polyol compound and the polythiol compound may be used in combination. With the combination use of the polyol compound and the polythiol compound, the refractive index of the dental restorative material of the present invention can be readily controlled, and the transparency thereof can be controlled. In the case where two or more different compounds are used for the polyol compound or the polythiol compound, or in the case where the polyol compound and the polythiol compound are used in combination, the distance (i.e., the number of main chain constituting atoms) used is the average value thereof. The average value herein can be calculated in such a manner that the value of "molar fraction of the component (i.e., the molar fraction with respect to the total of the components as 1)×number of main chain constituting atoms" is obtained for each of the components, and the values are summed.

In the polyol compound or the polythiol compound used, in the case where the polyol compound or the polythiol compound having no ring structure in the main chain structure is used in a larger molar number than the compound having a ring structure, the average value of the distance (i.e., the number of main chain constituting atoms) is preferably 2 to 6, and more preferably 2 to 4. In the case where the polyol compound or the polythiol compound having a ring structure in the main chain structure is used in a larger molar number than the compound having no ring structure, the average value of the distance (i.e., the number of main chain constituting atoms) is preferably 3 to 15, and more preferably 3 to 10.

The polyurethane resin after the reaction between the polyfunctional isocyanate compound and the polyol compound or the polythiol compound preferably has a chemical crosslinked structure therein for achieving a sufficient strength of the dental restorative material. Specifically, assuming that the average number of functional groups of the reactive groups per one molecule of the polyfunctional isocyanate compound is represented by A, and the average number of functional groups of the reactive groups per one molecule of the polyol compound or the polythiol compound is represented by B, $(A+B)/2 \geq 2.5$ is preferably satisfied, and $(A+B)/2 \geq 3.0$ is more preferably satisfied.

The polyol compound or the polythiol compound as the component (B) preferably has a radical polymerizable group in a molecule as a functional group that causes the chemical crosslinking. The radical polymerizable group herein means a functional group that performs polymerization through reaction with an initiator generating a radical. Preferred examples of the radical polymerizable group include a vinyl group, an acryloyloxy group, a methacryloyloxy group, and a styryl group. In the case where the compound has the radical polymerizable group in the molecule, crosslinks are formed through the reaction among the radical polymerizable groups, and the crosslinking density can be increased to enhance the water resistance. Even though the radical polymerizable group is not used for the crosslinking reaction, the remaining radical polymerizable group has higher hydrophobicity than a hydroxy group or a thiol group and thus does not impair the water resistance. The number of the radical polymerizable group in the molecule may be 1 to 4, and particularly preferably 1 to 2. In the case where the number of the radical polymerizable group exceeds 4, there is a tendency that the contraction in reaction becomes large.

The polyol compound or the polythiol compound as the component (B) preferably has compatibility with the polyfunctional isocyanate compound as the component (A). With the compatibility thereof, the progress of the polyaddition may not be impaired, and the dental restorative material having a high strength and high water resistance can be readily obtained.

The compatibility herein means that in the case where the component (A) and the component (B) are mixed to prepare a polymerizable composition, the component (A) and the component (B) can be in a uniform liquid state at room temperature (preferably 25° C.). Accordingly, at least one of the component (A) and the component (B) is necessarily in a liquid state at ordinary temperature (preferably 25° C.). The compatibility in terms of the absolute value of the difference of the octanol/water distribution coefficient (log P), which is an index of the hydrophilicity of the component (A) and the component (B) is preferably 5 or less, and more preferably 4 or less, from the standpoint that the curing is completed within a practical reaction time, unintended polyaddition may not occur in the curing, and a cured product having a high strength can be obtained. The value log P is a value that is calculated by the hydrophobic fragmental constant approach.

Examples of the polyol compound or the polythiol compound as the component (B) that can be preferably used in the present invention include the following.

Examples of the polyol compound having no ring structure in the main chain include an α,ω-alkanediol (such as butanediol, pentanediol, hexanediol, heptanediol, and octanediol), 2-butene-1,4-diol, neopentyl glycol, 2-butyl-2-ethyl-1,3-propanediol, 2,5-dimethyl-2,5-hexanediol, trimethylolpropane mono(meth)acrylate, glycerol mono(meth)acrylate, pentaerythritol di(meth)acrylate, an acid (e.g., (meth)acrylic acid) ring opening product of ethylene glycol diglycidyl ether, and pentaerythritol mono(meth)acrylate.

Examples of the polythiol compound having no ring structure in the main chain include an α,ω-alkanedithiol (such as butanedithiol, pentanedithiol, hexanedithiol, pentanedithiol, and octanedithiol), 2,3-butanedithiol, 3,6-oxa-1,8-octanedithiol, and ethylene bis(thioglycolate).

Examples of the polyol compound having a ring structure in the main chain include 1,3-bis(hexafluoro-α-hydroxyisopropyl)benzene, 2-benzyloxy-1,3-propanediol, adamantanediol, 1,4-cyclohexanedimethanol, 1,3-cyclopentanediol, 3-phenoxy-1,2-propanediol, adamantanetriol, tricyclodecanedimethanol, and an acid (e.g., (meth)acrylic acid and vinylbenzoic acid) ring opening product of bisphenol A diglycidyl ether.

Examples of the polythiol compound having a ring structure in the main chain include 4,5-bis(mercaptomethyl)-o-xylene, and 1,3,5-tris(3-mercaptobutyryloxyethyl)-1,3,5-triazin-2,4,6(1H,3H,5H)-trione.

These polyol compounds or the polythiol compounds may be used alone or as a mixture of different kinds thereof.

The polyol compound or the polythiol compound used is preferably the polyol compound from the standpoint of the odor.

The amount ratio of the component (A) and the component (B) in the polyurethane raw material polymerizable composition in terms of the ratio ($E_B/E_A$) of the total equivalent number ($E_B$) of the hydroxy groups derived from the component (B) with respect to the total equivalent number ($E_A$) of the isocyanate groups derived from the component (A) is preferably 0.8 to 1.4, and particularly preferably 0.9 to 1.2.

The polyfunctional isocyanate compound and the polyol compound or the polythiol compound may be used after forming into a prepolymer through reaction in advance, for the purposes of the easy handling and the suppression of the contraction in curing.

The polyurethane raw material polymerizable composition does not contain a urethane polymerization catalyst for facilitating the introduction of the crosslinked structure into the interior of the cured product. In the case where the polyurethane raw material polymerizable composition contains a urethane polymerization catalyst, the urethane bond forming reaction may rapidly proceed, and the flexibility of the molecule may also be rapidly lost, failing to form sufficient crosslinking Examples of the urethane polymerization catalyst that is not contained in the polyurethane raw material polymerizable composition include a tin catalyst, such as dibutyltin diacetate and dibutyltin dilaurate, an amine catalyst, such as triethylenediamine, and zirconium acetylacetonate.

The polyurethane raw material polymerizable composition may further contain as an arbitrary component (C) a radical polymerizable monomer having a radical polymerizable group (except for a radical polymerizable monomer having two or more hydroxy groups in a molecule) and/or (D) a polymerization initiator having activity to polymerization with the radical polymerizable group. The addition of these components may enable to control the properties of the polyurethane resin as the cured product. In particular, the addition of the component (C) can further enhance the crosslinking density since the flexibility of the molecule can be prevented from being decreased even when the urethane bond forming reaction proceeds. Accordingly, the component (C) is preferably in a liquid state at ordinary temperature of 25° C.

Examples of the radical polymerizable monomer that can be preferably used as the component (C) include vinyl acetate, acrylonitrile, methyl (meth)acrylate, glycidyl (meth)acrylate, cyclohexyl (meth)acrylate, benzyl (meth)acrylate, isobornyl (meth)acrylate, trifluoroethyl (meth)acrylate, dimethylacrylamide, styrene, butadiene, 2,2-bis(4-(meth)acryloyloxypolyethoxyphenyl)propane, diethylene glycol di(meth)acrylate, neopentyl glycol di(meth)acrylate, propylene glycol di(meth)acrylate, 1,6-bis(methacrylethyloxycarbonylamino)-2,2,4-trimethylhexane, divinylbenzene, trimethylolpropane tri(meth)acrylate, and pentaerythritol tetra(meth)acrylate.

The amount of the component (C) mixed may be appropriately determined, and is generally 1 to 20% by mass, and more preferably 2 to 10% by mass, based on the total mass of the polyurethane raw material polymerizable composition. In the case where the compound having a radical polymerizable group in a molecule is used as the component (B), the component (C) used preferably has the same radical polymerizable group as the radical polymerizable group of the component (B).

The component (D) added allows the radical polymerizable group of the component (B) and/or the component (C) to undergo reaction securely, so as to enable the enhancement of the crosslinking density. A thermal polymerization initiator and/or a photopolymerization initiator having been known may be used as the polymerization initiator without limitation. A thermal polymerization initiator is preferably used from the standpoint that the curing can be uniformly performed in the deeper portion. Specific examples of the preferred initiator include a peroxide initiator, such as benzoyl peroxide and tert-butyl peroxylaurate, and an azo initiator, such as azobisisobutyronitrile and azobis(2,4-dimethylvaleronitrile).

The amount of the polymerization initiator added is generally 0.005 to 1.0% by mass, preferably 0.01 to 0.5% by mass, and particularly preferably 0.01 to 0.1% by mass, based on the total mass of the polyurethane raw material polymerizable composition.

The thermal polymerization initiator used preferably has a 10-hour half-life temperature in a range of 40 to 150° C., and particularly preferably in a range of 50 to 100° C., from the standpoint of the handleability and the stability. In the case where the 10-hour half-life temperature is too low, there is a possibility that unintended radical polymerization reaction occurs, and in the case where the 10-hour half-life temperature is too high, the reaction temperature is necessarily higher, which causes a possibility that side reaction and coloration occur.

The resin matrix in the present invention may contain a resin other than the polyurethane resin, such as a (meth)acrylic resin, an epoxy resin, a urea resin, a polyester resin, a polyamide resin, and a polycarbonate resin. The content of the polyurethane resin based on the total amount of the resin matrix is preferably 50% by mass or more, more preferably 80% by mass or more, further preferably 95% by mass or more, and still further preferably 100% by mass.

The dental restorative material of the present invention can be obtained by curing the dental polymerizable composition containing the polyurethane raw material polymerizable composition and the inorganic filler.

The polyurethane raw material polymerizable composition may be cured by itself without the use of the inorganic filler, so as to provide a cured product. The cured product can be used as a dental material having a high strength in the oral cavity due to the excellent water resistance thereof.

<Inorganic Filler>

The dental restorative material of the present invention contains the inorganic filler. The inorganic filler is mixed from the standpoint of the enhancement of the mechanical strength of the dental restorative material of the present invention, the enhancement of the abrasion resistance by increasing the surface hardness thereof, and the enhancement of the cutting workability. The inorganic filler, such as inorganic particles, is used as the filler.

The inorganic filler is preferably at least one kind selected from the group consisting of silica, alumina, titania, zirconia, and a composite thereof. Specific examples of the inorganic particles include spherical particles and irregular particles of amorphous silica, silica-zirconia, silica-titania, silica-titania-zirconia, quartz, and alumina. The dental restorative material of the present invention preferably does not contain an inorganic salt, such as calcium carbonate, that may be dissolved in the environment in the oral cavity.

The inorganic filler may be added in the form of organic-inorganic composite particles. The organic-inorganic composite particles herein are a composite material formed of the inorganic particles described above and an organic resin.

The organic resin used in the organic-inorganic composite particles may be a known one without limitation. Specific examples thereof include a (meth)acrylic resin, a urethane resin, a urea resin, an epoxy resin, a polycarbonate resin, a polyamide resin, and a polyester resin, and a (meth)acrylic resin, a urethane resin, a urea resin, and an epoxy resin are preferred from the standpoint of the strength and the esthetics.

The average particle diameter of the inorganic filler is 0.001 to 100 μm from the standpoint of the abrasion resistance, the surface smoothness, and the retention of glossiness. The average particle diameter is preferably 0.01 to 20 μm.

The average particle diameter herein is the average value of the long diameters of the particles obtained through image analysis of the image obtained with a scanning or transmission electron microscope. In the case of calculating this value, for securing the measurement accuracy, at least 40 particles are necessarily measured, and 100 or more particles are preferably measured.

The preferred amount of the inorganic filler mixed in the dental restorative material of the present invention is 25 to 1,000 parts by mass, and preferably 50 to 600 parts by mass, per 100 parts by mass of the resin matrix.

In the dental restorative material of the present invention, the inorganic filler preferably has a refractive index that is close to the refractive index of the polyurethane resin as the resin matrix from the standpoint of the esthetics. Specifically, the refractive index of the inorganic filler is preferably 1.2 to 1.8, and more preferably 1.4 to 1.6. Therefore, amorphous silica, silica-zirconia, silica-titania, silica-titania-zirconia, quartz, and the like each having a refractive index within the range are preferably used. The transparency of the dental restorative material can be controlled to opaque by mixing a pigment, specifically a white pigment, such as zinc oxide or titanium oxide. Therefore, in the case where the dental restorative material is transparent in the state where no pigment is mixed therein, the transparency can be freely controlled to a target extent, resulting in a prosthesis excellent in esthetics.

The transparency of the dental restorative material is preferably in a range of 0.1 to 0.6, and more preferably in a range of 0.2 to 0.5, in which the transparency can be controlled in such a range that two layers of the transparent enamel and the relatively opaque dentin can be expressed with a single curable composition, resulting in a prosthesis excellent in esthetics. The transparency can be obtained by the following expression after measuring the Y value of the tristimulus values in the XYZ color coordinate system with black background and white background.

(transparency)=(Y value on black background)/(Y value on white background)

The shape of the inorganic filler is particularly preferably a spherical shape since a resin composition that is particularly excellent in the abrasion resistance, the surface smoothness, and the retention of glossiness can be obtained. The spherical shape herein means that the average evenness obtained through image analysis of the image obtained with a scanning or transmission electron microscope is 0.6 or more. The average evenness is more preferably 0.7 or more, and further preferably 0.8 or more. The average evenness in the image analysis of the image obtained with a scanning or transmission electron microscope can be calculated by the following expression after obtaining the number of particles (n), the long diameter (Li) as the maximum diameter of the particle, and the short diameter (Bi) as the diameter perpendicular to the long diameter.

$$\text{average evenness} = \frac{\sum_{i=1}^{n} Bi/Li}{n}$$

For securing the measurement accuracy in the calculation of the value, at least 40 particles are necessarily measured, and 100 or more particles are preferably measured.

The inorganic filler is preferably subjected to a surface treatment for enhancing the affinity to the polyurethane raw material polymerizable composition, eventually the polyurethane resin matrix, so as to enhance the mechanical strength and the water resistance. The surface treating agent used is generally a silane coupling agent, and the effect of the surface treatment with a silane coupling agent is particularly high for the inorganic particle filler based on silica. The surface treatment may be performed by a known method, and preferred examples of the silane coupling agent used include methyltrimethoxysilane, methyltriethoxysilane, hexamethylclisilazane, vinyltrimethoxysilane, 3-methacryloyloxypropyltrimethoxysilane, 3-glycidoxypropyltrimethoxysilane, 3-glycidoxypropylmethyldimethoxysilane, 3-glycidoxypropyltriethoxysilane, 2-(3,4-epoxycyclohexyl)ethyltrimethoxysilane, N-2-(aminoethyl)-3-aminopropylmethyldimethoxysilane, N-2-(aminoethyl)-3-aminopropyltrimethoxysilane, N-2-(aminoethyl)-3-aminopropyltriethoxysilane, 3-aminopropyltrimethoxysilane, 3-aminopropyltriethoxysilane, N-(3-triethoxysilylpropyl)-4-hydroxybutylamide, N-(3-triethoxysilylpropyl)-O-polyoxyethylene oxide urethane, 3-mercaptoprpoyltrimethoxysilane, and 3-isocyanatopropyltriethoxysilane. A silane coupling agent that has a chemical bond to the polyurethane raw material polymerizable composition or the polyurethane resin matrix is particularly preferred, and examples thereof include N-2-(aminoethyl)-3-aminopropylmethyldimethoxysilane, N-2-(aminoethyl)-3-aminopropyltrimethoxysilane, N-2-(aminoethyl)-3-aminopropyltriethoxysilane, 3-aminopropyltrimethoxysilane, 3-aminopropyltriethoxysilane, N-(3-triethoxysilylpropyl)-4-hydroxybutylamide, N-(3-triethoxysilylpropyl)-O-polyoxyethylene oxide urethane, 3-mercaptoprpoyltrimethoxysilane, and 3-isocyanatopropyltriethoxysilane. The silane coupling agent may be used alone or as a combination of two or more kinds thereof.

The dental restorative material of the present invention may contain a filler other than the inorganic filler depending on purpose. Specific examples thereof include organic particles, such as polymethyl methacrylate particles, polyethyl methacrylate particles, and a hyperbranched polymer, and organic fibers, such as cellulose fibers and carbon nanofibers.

The dental restorative material of the present invention can be applied to a resin material for dental cutting work, a resin material for a dental plate, an orthodontic material, and a material for a mouth guard, and is particularly preferably applied to a resin material for dental cutting work.

[Dental Polymerizable Composition]

The dental restorative material of the present invention can be formed by curing through polymerization of the dental polymerizable composition. The dental polymerizable composition preferably contains the polyurethane raw material polymerizable composition and the inorganic filler described above.

The dental polymerizable composition of the present invention may contain an arbitrary component corresponding to the purpose added thereto depending on the embodiment of the dental restorative material of the present invention. Examples of the component include a fluorescent agent, an ultraviolet ray absorbent, an antioxidant, a pigment, an antibacterial agent, and an X-ray contrast medium. The amount thereof added may be appropriately determined depending on the purpose.

In the method for producing a dental restorative material of the present invention, cast polymerization is preferably employed. Specifically, the method may include at least a step of preparing a dental polymerizable composition containing the polyfunctional isocyanate compound as the component (A), the polyol compound or the polythiol compound as the component (B), and the inorganic filler, and a step of casting the dental polymerizable composition in a mold and then polymerization curing the composition.

In the step of preparing the dental polymerizable composition, the polymerizable composition can be produced by mixing the necessary amounts of the components. A method of mixing the inorganic filler with a mixture (formed of a composition that does not contain the inorganic filler) prepared in advance, for example, by a method of agitation mixing the polyfunctional isocyanate compound as the component (A) and the polyol compound or the polythiol compound as the component (B), so as to prepare the dental polymerizable composition (method 1) may be employed, and a method of preparing separate compositions containing the polyfunctional isocyanate compound as the component (A) and the polyol compound or the polythiol compound as the component (B) respectively, mixing the inorganic filler with any one or both of the compositions to prepare a composition (a) containing the polyfunctional isocyanate compound and a composition (b) containing the polyol compound or the polythiol compound, and then mixing the compositions (a) and (b) to prepare the dental polymerizable composition (method 2) may also be employed. The dental polymerizable composition in the method 2 is such a dental polymerizable composition that is prepared by mixing the composition (a) containing the polyfunctional isocyanate compound and the composition (b) containing the polyol compound or the polythiol compound, in which at least one composition of the composition (a) and the composition (b) contains the inorganic filler.

The method 2 is preferably employed from the standpoint of the reactivity of the polyfunctional isocyanate compound and the polyol compound or the polythiol compound.

In the method 1, the method of mixing the polyfunctional isocyanate compound as the component (A) and the polyol compound or the polythiol compound as the component (B) in advance is not particularly limited, and for example, such a method may be employed that the polyfunctional isocyanate compound and the polyol compound or the polythiol compound are added to each other and the resultant is subjected to agitation mixing with a magnetic stirrer, an agitation blade, a centrifugal mixer, or the like until an uniform mixture is obtained. The method of mixing the inorganic filler with the resulting mixture to provide the dental polymerizable composition is also not particularly limited, and the dental polymerizable composition may be prepared by adding the inorganic filler to the mixed polyfunctional isocyanate compound and the polyol compound or the polythiol compound, and mixing the components with a crushing mixer, a planetary mixer, a centrifugal mixer, or the like. The dental polymerizable composition prepared in this manner is preferably subjected to a defoaming treatment for removing bubbles contained therein before the polymerization curing. The defoaming treatment used may be a known method, and such a method as pressurizing defoaming, vacuum defoaming, and centrifugal defoaming, may be arbitrarily employed.

In the method 2, the method of mixing the inorganic filler with the polyfunctional isocyanate compound as the component (A) or the polyol compound or the polythiol compound as the component (B) is not particularly limited, and the components may be mixed with a crushing mixer, a planetary mixer, a centrifugal mixer, or the like, so as to prepare the compositions (a) and (b). The compositions (a) and (b) prepared in this manner are preferably subjected to a defoaming treatment for removing bubbles contained therein before mixing the compositions. The defoaming treatment used may be a known method, and such a method as pressurizing defoaming, vacuum defoaming, and centrifugal defoaming, may be arbitrarily employed.

The method of mixing the composition (a) containing the isocyanate compound and the composition (b) containing the polyol compound or the polythiol compound to prepare the dental polymerizable composition is not particularly limited, and such a mixing device as a static mixer or a rotation-revolution mixer is preferably used for preventing bubbles from being mixed therein.

In the present invention, for polymerization curing of the dental polymerizable composition obtained above into a target shape, cast molding of filling the composition in a mold and then polymerization curing the composition is preferably performed. The mold used in casting is not particularly limited, and ones having a rectangular column shape, a cylindrical shape, a rectangular plate shape, a circular disk shape, and the like may be appropriately used corresponding to the shape assumed in advance for the product forms. The size thereof may be such a size that the polymerized product has the assumed shape in consideration of the shrinkage and the like, or may be such a large size that estimates the working margin assuming the working after the polymerization.

The method of casting the dental polymerizable composition in the mold is not particularly limited, and a known method may be used. The entrainment of bubbles in the dental restorative material of the present invention is not preferred from the standpoint of the strength and the esthetics, and therefore bubbles included in the dental polymerizable composition are preferably removed. Therefore, pressure casting and vacuum casting are preferably performed.

In the step of polymerization curing, the method of polymerization curing the dental polymerizable composition of the present invention to produce the dental restorative material of the present invention is not particularly limited, and in the case where the dental restorative material of the present invention is used as a resin material for dental cutting work, the dental polymerizable composition preferably contains the polyol compound or the polythiol compound having a radical polymerizable group as the component (B) and/or the component (C), and is preferably produced in the following manner, from the standpoint of the achievement of the dental restorative material having a high strength with high water resistance imparted thereto. Specifically, such a method is preferably employed that the dental polymerizable composition is cast and then heated, and during heating, the formation of the urethane bond and the radical polymerization of the radical polymerizable group are performed. The heating is preferably performed through a single heating step. The single heating step means that the process including heating and cooling is not performed twice or more, and stepwise heating without cooling, for example, the composition is retained at a certain temperature after heating, and then again heated, is designated as the single heating step. The dental restorative material is preferably produced in such a manner that the dental polymerizable composition is cured by heating through a single heating step, in which the formation of the urethane bond and the radical polymerization of the radical polymerizable group are performed.

In the single heating step, the aforementioned stepwise heating is preferred since the stress in curing can be suppressed to provide the dental restorative material having less defects.

The dental polymerizable composition does not contain a urethane polymerization catalyst, and therefore is cured by heating for polymerization after casting. The composition generates heat through reaction heat in polymerization, and therefore the temperature (curing temperature) is preferably controlled in heating. Specifically, the temperature is preferably controlled to prevent from exceeding 150° C. from the standpoint that the polymerization curing proceeds at an industrially allowable rate, stress and cracks due to the rapid reaction are prevented from occurring in the cured product, and the monomer is prevented from being deteriorated.

In the polymerization curing by heating in the step of polymerization curing, the composition may be pressurized for suppressing the formation of voids due to bubbles in the cured product (i.e., the dental restorative material). The method of pressurizing is not particularly limited, and the composition may be mechanically pressurized or may be pressurized with gas, such as nitrogen.

The cured product obtained through the polymerization by heating may be taken out from the mold, and then may be subjected to a treatment, such as a heat treatment for relaxing the residual stress, cutting work and grinding for modifying into a necessary shape or a convenient shape. Furthermore, a fixture, such as a pin, for fixing to a CAD/CAM system may be bonded thereto to provide a resin block for dental cutting work.

EXAMPLES

The present invention will be described specifically with reference to Examples and Comparative Examples below, but the present invention is not limited thereto. The abbreviated names or the abbreviated symbols and the structural formula or the substance name of the substances used for producing specimens of Examples and Comparative Examples, and the preparation methods and the evaluation methods of the specimens are described below.

The three-point bending strength (BS), the surface hardness, the cutting workability, and the transparency of the dental restorative materials of Examples and Comparative Examples described later were evaluated in the following manners. The three-point bending strength ($BS_A$), the three-point bending strength after water immersion ($BS_W$), and the compatibility of the polyol compound or the polythiol compound and the polyfunctional isocyanate compound for the polyurethane resins (i.e., the cured products of the polyurethane raw material polymerizable compositions) used in Examples and Comparative Examples were evaluated in the following manners.

<Evaluation of Dental Restorative Material>

1. Three-Point Bending Strength (BS)

The dental restorative material obtained by the method described later was cut out with a low-speed diamond cutter (produced by Buehler Ltd.) and prepared with #2000 water resistant abrasive paper to a rectangular column shape of 1.2 mm×4.0 mm×14.0 mm, so as to provide a test piece. The test piece was mounted on Autograph (produced by Shimadzu Corporation), and subjected to a three-point bending test under condition of a supporting point span of 12.0 mm and a crosshead speed of 1.0 mm/min.

The bending strength BS was calculated according to the following expression (1). 10 test pieces were produced for each of Examples and Comparative Examples, and the average value thereof was designated as the bending strength of the dental restorative material.

$$BS = 3PS/2WB^2 \quad (1)$$

In the expression, P represents the bending load at the maximum point (N), S represents the supporting point span (12.0 mm), W represents the width (i.e., a measured value, which was approximately 4.0 mm), and B represents the thickness (i.e., a measured value, which was approximately 1.2 mm).

2. Evaluation of Surface Hardness

The dental restorative material obtained by the method described later was cut out with a low-speed diamond cutter (produced by Buehler Ltd.) and prepared with #1500 water resistant abrasive paper and 0.3 μm alumina particles to a rectangular column shape of 12 mm×14 mm×1.0 mm, so as to provide a test piece. The surface hardness of the test piece was obtained by measuring the diagonal point length (d, unit: μm) of a dent formed under a load condition of 100 gf and 30 seconds was measured with a microhardness meter (MHT-1, produced by Matsuzawa Co., Ltd.). The surface hardness Hv was obtained according to the following expression (2).

$$Hv = 1854.37 \times 100/d^2 \quad (2)$$

3. Evaluation of Cutting Workability

The dental restorative material obtained by the method described later was mounted on a low-speed diamond cutter (produced by Buehler Ltd.) to enable to cut a surface of 12 mm×14 mm. The material was cut under a load of 200 gf, and the period of time until completing the cutting operation was evaluated. The cutting workability was evaluated based on the resulting working time.

4. Evaluation of Transparency

The dental restorative material obtained by the method described later was cut out with a low-speed diamond cutter (produced by Buehler Ltd.) and prepared with #1500 water resistant abrasive paper and 0.3 μm alumina particles to a rectangular column shape of 12 mm×14 mm×1.0 mm, so as to provide a test piece. The resulting test piece was measured for the Y value of the tristimulus values on black background and white background with a colorimeter (TC-1800 MKII, produced by Tokyo Denshoku Co., Ltd.). The value of the following expression (3) was designated as the transparency. The transparencies of the dental restorative materials are shown in Table 1 described later.

$$(\text{transparency}) = (Y \text{ value on black background})/(Y \text{ value on white background}) \quad (3)$$

<Evaluation of Polyurethane Resin (Cured Product of Polyurethane Raw Material Polymerizable Composition)>

5. Three-Point Bending Strength ($BS_A$)

The polyurethane resin (i.e., the cured product of the polyurethane raw material polymerizable composition) used in each of Examples and Comparative Examples was cut out with a low-speed diamond cutter (produced by Buehler Ltd.) and prepared with #2000 water resistant abrasive paper to a rectangular column shape of 1.2 mm×4.0 mm×14.0 mm, so as to provide a test piece. The test piece was measured for the three-point bending strength under the condition described in the item 1 above.

The polyurethane resin was prepared in the following manner.

The polyfunctional isocyanate compound, the polyol compound or the polythiol compound, the radical polymerizable monomer, and the radical polymerization catalyst used in each of Examples and Comparative Examples were stirred and mixed in the amount ratios used in each of Examples and Comparative Examples with a magnetic stirrer, so as to prepare a polyurethane raw material polymerizable composition. Subsequently, the polyurethane raw material polymerizable composition was cast in a mold having a length of 12, a width of 18, and a thickness of 14 (mm). The composition was allowed to stand at 33° C. under nitrogen pressure (0.3 MPa) for 15 hours. Thereafter, under the pressurized state maintained, the composition was heated to 80° C., retained for 3 hours, and then heated to 120° C., followed by further retaining for 3 hours. Thereafter, the cured product was taken out from the mold to provide the polyurethane resin.

6. Three-Point Bending Strength after Water Immersion ($BS_W$)

The polyurethane resin (i.e., the cured product of the polyurethane raw material polymerizable composition) used in each of Examples and Comparative Examples was cut out with a low-speed diamond cutter (produced by Buehler Ltd.) and prepared with #2000 water resistant abrasive paper to a rectangular column shape of 1.2 mm×4.0 mm×14.0 mm, so as to provide a test piece. The test piece was stored in ion exchanged water at 37° C. for one week. The test piece was taken out, and after removing water on the surface thereof, was measured for the three-point bending strength under the condition described in the item 1 above. The results are shown in Table 1 described later. The polyurethane resin was prepared in the same manner as in the item 5 above.

7. Evaluation of Compatibility of Polyol Compound or Polythiol Compound and Polyfunctional Isocyanate Compound The polyfunctional isocyanate compound, the polyol compound or the polythiol compound, the radical polymerizable monomer, and the radical polymerization catalyst used in each of Examples and Comparative Examples were stirred and mixed in the amount ratios used in each of Examples and Comparative Examples with a magnetic stirrer at 25° C. for 3 hours. The mixture was observed for the appearance, and the case where the mixture was a uniform liquid was evaluated as G, whereas the case where the mixture was separated was evaluated as B.

The octanol/water distribution coefficient (log P (a)) of the polyfunctional isocyanate compound and the octanol/water distribution coefficient (log P (b)) of the polyol compound or the polythiol compound in each of Examples and Comparative Examples were calculated by the hydrophobic fragmental constant approach, and the absolute value of the difference between these values is calculated and designated as the index of the compatibility.

Materials Used in Examples and Comparative Examples

1. Polyfunctional Isocyanate Compound
TDI: tolylene diisocyanate (2,4-: approximately 80%, 2,6-: approximately 20%) (molecular weight: 174, number of functional groups: 2)
XDI: m-xylylene diisocyanate (molecular weight: 188, number of functional groups: 2)
TMXDI: 1,3-bis(2-isocyanato-2-propyl)benzene (molecular weight: 244, number of functional groups: 2)
2. Polyol Compound or Polythiol Compound
GTP: glycerol tripropoxylate (average molecular weight: 266, number of functional groups: 3, number of main chain constituting atoms: 9)
PETP: pentaerythritol tetrapropoxylate (average molecular weight: 426, number of functional groups: 4, number of main chain constituting atoms: 9)
PEMA: pentaerythritol tetra(mercaptoacetate) (molecular weight: 432, number of functional groups: 4, number of main chain constituting atoms: 9)
GLM: glycerol monomethacrylate (molecular weight: 160, number of functional groups: 2, containing methacryloyloxy group, number of main chain constituting atoms: 2)
bis-GMA: bisphenol A glycidyl dimethacrylate (molecular weight: 513, number of functional groups: 2, containing methacryloyloxy group, number of main chain constituting atoms: 19)
TMP: trimethylolpropane (molecular weight: 134, number of functional groups: 3, number of main chain constituting atoms: 3)
3. Inorganic Filler
F1: silica-zirconia (spherical shape, average particle diameter: 0.2 μm, surface treated with 3-aminopropyltrimethoxysilane, average evenness: 0.94)
F2: silica-zirconia (spherical shape, average particle diameter: 0.2 μm, surface treated with 3-methacryloyloxypropyltrimethoxysilane, average evenness: 0.94)
F3: silica-zirconia (spherical shape, average particle diameter: 0.2 μm, surface treated with 1/1 mixture of 3-aminopropyltrimethoxysilane and 3-methacryloyloxypropyltrimethoxysilane, average evenness: 0.94)
4. Radical Polymerization Catalyst
PBL: t-butyl peroxylaurate (10-hour half-life temperature: 98° C.)
V65: 2,2'-azobis(2,4-dimethylvaleronitrile) (10-hour half-life temperature: 51° C.)
BPO: benzoyl peroxide (10-hour half-life temperature: 74° C.)
5. Radical Polymerizable Monomer
UDMA: 1,6-bis(methacrylethyloxycarbonylamino)-2,2,4-trimethylhexane
TEGDMA: triethylene glycol dimethacrylate
NPG: neopentyl glycol dimethacrylate Example 1

240 g of TDI and 160 g of F1 were placed in a planetary mixer (produced by Inoue Mfg., Inc.), and kneaded to provide a composition (a). Similarly, 240 g of GTP and 160 g of F1 were placed in a planetary mixer (produced by Inoue Mfg., Inc.), and kneaded to provide a composition (b). The resulting compositions were placed in a desiccator, and depressurized for 60 minutes to remove bubbles in the compositions. The compositions were filled in mixing cartridges (CDA, produced by Mixpac Systems AG). The cartridges were mounted on a mixer syringe (MA 4.0-17S, produced by Mixpac Systems AG), and a dental polymerizable composition as a mixture of the compositions (a) and (b) was filled in a mold having a length of 12, a width of 18, and a thickness of 14 (mm), and then allowed to stand at 23° C. under nitrogen pressure (0.3 MPa) for 1 hour. Thereafter, under the pressurized state maintained, the composition was heated to 150° C. over 20 hours, and retained for 6 hours. Thereafter, the cured product was taken out from the mold to provide a dental restorative material. The evaluation results are shown in Table 1.

Example 2

A dental restorative material was obtained in the same manner as in Example 1 except that in Example 1 320 g of TDI and 80 g of F1 were used for the composition (a), and 320 g of GTP and 80 g of F1 were used for the composition (b). The evaluation results are shown in Table 1.

Example 3

A dental restorative material was obtained in the same manner as in Example 1 except that in Example 1 240 g of XDI and 160 g of F1 were used for the composition (a), and 200 g of PETP and 200 g of F1 were used for the composition (b). The evaluation results are shown in Table 1.

Example 4

A dental restorative material was obtained in the same manner as in Example 1 except that in Example 1 240 g of XDI and 160 g of F1 were used for the composition (a), and 240 g of PEMA and 160 g of F1 were used for the composition (b). The evaluation results are shown in Table 1.

Example 5

6.2 g of GLM and 8.9 g of F1 were placed in an agitation vessel, and kneaded with a rotation-revolution mixer (produced by Kurabo Industries, Ltd.). Subsequently, 7.2 g of XDI and 0.01 g of PBL were placed therein, and kneaded with the rotation-revolution mixer to prepare a dental polymerizable composition. The resulting dental polymerizable composition was filled in a mold having a length of 12, a width of 18, and a thickness of 14 (mm), and then allowed to stand at 33° C. under nitrogen pressure (0.3 MPa) for 15 hours. Thereafter, under the pressurized state maintained, the composition was heated to 80° C. and retained for 3 hours, and further heated to 120° C. and retained for 3 hours. Thereafter, the cured product was taken out from the mold to provide a dental restorative material formed of the cured product of the dental resin composition. The evaluation results are shown in Table 1.

Example 6

A dental restorative material was obtained in the same manner as in Example 5 except that 4.3 g of GLM and 13.9 g of F1 were placed in an agitation vessel, and kneaded with a rotation-revolution mixer (produced by Kurabo Industries, Ltd.), and subsequently 5.0 g of XDI and 0.01 g of V65 were placed therein, and kneaded with the rotation-revolution mixer to prepare a dental polymerizable composition. The evaluation results are shown in Table 1.

Example 7

A dental restorative material was obtained in the same manner as in Example 5 except that 4.0 g of GLM and 10.0 g of F1 were placed in an agitation vessel, and kneaded with a rotation-revolution mixer (produced by Kurabo Industries, Ltd.), and subsequently 6.0 g of TMXDI and 0.01 g of PBL were placed therein, and kneaded with the rotation-revolution mixer to prepare a dental polymerizable composition. The evaluation results are shown in Table 1.

Example 8

A dental restorative material was obtained in the same manner as in Example 5 except that 5.1 g of GLM, 0.5 g of NPG, and 7.8 g of F3 were placed in an agitation vessel, and kneaded with a rotation-revolution mixer (produced by Kurabo Industries, Ltd.), and subsequently 6.0 g of XDI and 0.01 g of PBL were placed therein, and kneaded with the rotation-revolution mixer to prepare a dental polymerizable composition. The evaluation results are shown in Table 1.

Example 9

A dental restorative material was obtained in the same manner as in Example 5 except that 3.4 g of GLM, 2.8 g of bis-GMA, and 9.1 g of F3 were placed in an agitation vessel, and kneaded with a rotation-revolution mixer (produced by Kurabo Industries, Ltd.), and subsequently 7.4 g of XDI and 0.01 g of PBL were placed therein, and kneaded with the rotation-revolution mixer to prepare a dental polymerizable composition. The evaluation results are shown in Table 1.

Example 10

A dental restorative material was obtained in the same manner as in Example 5 except that 4.3 g of GLM, 0.5 g of TMP, and 7.2 g of F3 were placed in an agitation vessel, and kneaded with a rotation-revolution mixer (produced by Kurabo Industries, Ltd.), and subsequently 6.0 g of XDI and 0.01 g of PBL were placed therein, and kneaded with the rotation-revolution mixer to prepare a dental polymerizable composition. The evaluation results are shown in Table 1.

Example 11

A dental restorative material was obtained in the same manner as in Example 5 except that 2.2 g of GLM, 3.7 g of GTP, and 8.4 g of F3 were placed in an agitation vessel, and kneaded with a rotation-revolution mixer (produced by Kurabo Industries, Ltd.), and subsequently 6.6 g of XDI and 0.01 g of PBL were placed therein, and kneaded with the rotation-revolution mixer to prepare a dental polymerizable composition. The evaluation results are shown in Table 1.

Comparative Example 1

180 g of UDMA and 60 g of TEGDMA were mixed. 2.4 g of BPO as a thermal polymerization initiator was added, and stirred to provide a solution 1. 240 g of the solution 1 and 160 g of F2 were placed in a planetary mixer (produced by Inoue Mfg., Inc.), and kneaded to provide a dental polymerizable composition.

The resulting dental polymerizable composition was placed in a desiccator, and depressurized for 60 minutes to remove bubbles in the composition. The resulting dental polymerizable composition was filled in a mold having a length of 12, a width of 18, and a thickness of 14 (mm), and then allowed to stand at 23° C. under nitrogen pressure (0.3 MPa) for 1 hour. Thereafter, under the pressurized state maintained, the composition was heated to 150° C. over 20 hours, and retained for 6 hours. Thereafter, the cured product was taken out from the mold to provide a dental restorative material. The evaluation results are shown in Table 2.

Comparative Example 2

10 g of TDI and 10 g of GTP were mixed with a magnetic stirrer, and then filled in a mold having a length of 12, a width of 18, and a thickness of 14 (mm). The composition was allowed to stand at 23° C. under nitrogen pressure (0.3 MPa) for 1 hour, and then under the pressurized state maintained, was heated to 150° C. over 20 hours, and retained for 6 hours. Thereafter, the cured product was taken out from the mold to provide a dental restorative material. The evaluation results are shown in Table 2.

Comparative Example 3

5.0 g of TMP and 10 g of TMXDI were added to each other and stirred with a magnetic stirrer. The components were stirred at 30° C. for 3 hours, but were not compatible with each other.

TABLE 1

| | | | Example | | | | | | | | | | |
|---|---|---|---|---|---|---|---|---|---|---|---|---|---|
| | | | 1 | 2 | 3 | 4 | 5 | 6 | 7 | 8 | 9 | 10 | 11 |
| Dental restorative material | Polyurethane raw material polymerizable composition (raw materials of resin matrix) | Polyfunctional isocyanate compound | TDI | TDI | XDI | XDI | XDI | XDI | TMXDI | XDI | XDI | XDI | XDI |
| | | Polyol compound or polythiol compound | GTP | GTP | PETP | PEMA | GLM | GLM | GLM | GLM | GLM bis-GMA | GLM TMP | GLM GTP |
| | | Radical polymerizable monomer | — | — | — | — | — | — | — | NPG | — | — | — |
| | | Radical polymerization catalyst | — | — | — | — | PBL | V65 | PBL | PBL | PBL | PBL | PBL |
| | Inorganic filler | | F1 | F1 | F1 | F1 | F1 | F1 | F1 | F3 | F3 | F3 | F3 |

TABLE 1-continued

|  |  | Example | | | | | | | | | | |
|---|---|---|---|---|---|---|---|---|---|---|---|---|
|  |  | 1 | 2 | 3 | 4 | 5 | 6 | 7 | 8 | 9 | 10 | 11 |
|  | Part by mass of inorganic filler per 100 parts by mass of resin matrix | 67 | 25 | 82 | 67 | 66 | 149 | 100 | 67 | 67 | 67 | 67 |
|  | Number of main chain constituting atoms | 9.0 | 9.0 | 9.0 | 9.0 | 2.0 | 2.0 | 2.0 | 2.0 | 4.6 | 2.1 | 5.5 |
| Evaluation | Bending strength (MPa) | 176 | 169 | 184 | 188 | 278 | 283 | 255 | 298 | 277 | 287 | 249 |
|  | Surface hardness (Hv) | 35 | 29 | 34 | 31 | 44 | 70 | 52 | 45 | 47 | 44 | 40 |
|  | Cutting workability (sec) | 86 | 98 | 84 | 88 | 78 | 70 | 70 | 72 | 75 | 74 | 82 |
|  | Transparency | 0.26 | 0.25 | 0.31 | 0.48 | 0.29 | 0.30 | 0.32 | 0.28 | 0.27 | 0.30 | 0.27 |
| Compatibility | logP (a) of polyfunctional isocyanate compound | 3.38 | 3.38 | 3.43 | 3.43 | 3.43 | 3.43 | 4.22 | 3.43 | 3.43 | 3.43 | 3.43 |
|  | logP (b) of polyol compound or polythiol compound | −1.31 | −1.31 | −0.94 | 1.87 | −0.082 | −0.082 | −0.082 | −0.082 | 4.81 | −0.13 | −0.285 |
|  | Absolute value of difference of logP (a) and logP (b) | 4.69 | 4.69 | 4.37 | 1.56 | 3.51 | 3.51 | 4.30 | 3.51 | 1.38 | 3.56 | 3.71 |
|  | Compatibility test result | G | G | G | G | G | G | G | G | G | G | G |
|  | Thee-point bending strength $BS_A$ (MPa) of cured product of polyurethane raw material polymerizable composition | 174 | 174 | 176 | 214 | 272 | 304 | 252 | 317 | 276 | 306 | 241 |
|  | Thee-point bending strength after water immersion $BS_W$ (MPa) of cured product of polyurethane raw material polymerizable composition | 11 | 11 | 53 | 186 | 227 | 251 | 212 | 268 | 243 | 264 | 193 |
|  | $BS_A/BS_W$ | 0.06 | 0.06 | 0.30 | 0.87 | 0.83 | 0.83 | 0.84 | 0.85 | 0.88 | 0.86 | 0.80 |

TABLE 2

|  |  |  |  | Comparative Example | | |
|---|---|---|---|---|---|---|
|  |  |  |  | 1 | 2 | 3 |
| Dental restorative material | Polyurethane raw material polymerizable composition (raw materials of resin matrix) | Isocyanate compound | | — | TDI | TMXDI |
|  |  | Polyol compound or polythiol compound | | — | GTP | TMP |
|  |  | Radical polymerizable monomer | | UDMA TEGDMA | — | — |
|  |  | Radical polymerization catalyst | | BPO | — | — |
|  | Inorganic filler | | | F2 | — | — |
|  | Part by mass of inorganic filler per 100 parts by mass of resin matrix | | | 67 | 0 | — |
|  | Distance between two hydroxyl groups or distance between two thiol groups (number of atoms) | | | — | 9.0 | — |
| Evaluation | Bending strength (MPa) | | | 132 | 174 | — |
|  | Surface hardness (Hv) | | | 33 | 16 | — |
|  | Cutting workability (sec) | | | 89 | 123 | — |
|  | Transparency | | | 0.20 | 0.12 | — |
|  | Compatibility | logP (a) of polyfunctional isocyanate compound | | — | 3.38 | 4.22 |
|  |  | logP (b) of polyol compound or polythiol compound | | — | −1.31 | −0.975 |
|  |  | Absolute value of difference of logP (a) and logP (b) | | — | 4.69 | 5.20 |
|  |  | Compatibility test result | | — | G | B |
|  | Thee-point bending strength $BS_A$ (MPa) of cured product of polyurethane raw material polymerizable composition | | | — | 174 | — |

TABLE 2-continued

| | Comparative Example | | |
|---|---|---|---|
| | 1 | 2 | 3 |
| Thee-point bending strength after water immersion $BS_W$ (MPa) of cured product of polyurethane raw material polymerizable composition | — | 11 | — |
| $BS_A/BS_W$ | — | 0.06 | — |

It is understood from the comparison between Examples 1 to 11 and Comparative Example 1 that the dental restorative material of the present invention has a higher bending strength than the dental restorative material formed of the methacrylic resin, and has a transparency equivalent thereto. It is understood from the comparison between Examples 1 to 11 and Comparative Example 2 that the addition of the inorganic filler enhances the surface hardness and the cutting workability. It is understood from the comparison between Examples 1 and 2 that with a larger amount of the inorganic filler, the surface hardness is higher, and the cutting workability is enhanced. It is understood from the comparison between Examples 1 to 4 and Examples 5 to 11 that with the functional group enhancing the compatibility in the polyol compound or the polythiol compound, a higher bending strength is obtained. It is understood from the comparison between Examples 5 and 8 that with the radical polymerizable monomer contained, a higher bending strength is obtained.

It is understood from the comparison between Examples 5 and 10 that with the composition capable of introducing chemical crosslinking in the formation of polyurethane, a higher bending strength is obtained. It is understood from the comparison between Examples 1, 5, and 11 that with a smaller distance between the functional groups, a higher bending strength is obtained.

As described above, the dental restorative material of the present invention had a high bending strength and a high surface hardness, and was excellent in transparency and cutting workability. It was found that the polyurethane resin having a high strength excellent in water resistance was produced in the case where the polyol or polythiol having a number of main chain constituting atoms within the particular range was used. Accordingly, it was found that the dental restorative material containing the polyurethane resin similarly was excellent in water resistance and retained the high strength in the oral cavity.

The invention claimed is:

1. A polyurethane raw material polymerizable composition comprising:
   (A) a polyfunctional isocyanate compound and
   (B) a polyol compound having at least two hydroxy groups in a molecule or a polythiol compound having at least two thiol groups in a molecule, the polyol compound or the polythiol compound having a distance between the most remote two hydroxy groups or thiol groups in terms of a number of atoms constituting a main chain of a divalent organic residual group intervening between the two hydroxy groups or thiol groups of 2 to 8 in the case where the organic residual group has no ring structure in the main chain, or 3 to 20 in the case where the organic residual group has a ring structure in the main chain provided that all atoms constituting a ring of the ring structure are included in the atoms constituting the main chain, and
   not comprising a urethane polymerization catalyst,
   wherein the polyol compound or the polythiol compound (B) contains a polyol compound or a polythiol compound having a radical polymerizable group in a molecule.

2. The polyurethane raw material polymerizable composition according to claim 1, wherein the polyol compound or the polythiol compound (B) has compatibility with the polyfunctional isocyanate compound.

3. The polyurethane raw material polymerizable composition according to claim 1, wherein the polyurethane raw material polymerizable composition further comprises (C) a radical polymerizable monomer having a radical polymerizable group (except for a polyol compound and a polythiol compound each having a radical polymerizable group in a molecule).

4. The polyurethane raw material polymerizable composition according to claim 1, wherein the polyurethane raw material polymerizable composition further comprises (D) a polymerization initiator for the radical polymerizable group.

5. A dental polymerizable composition comprising the polyurethane raw material polymerizable composition according to claim 1 and an inorganic filler.

6. A method for producing a dental restorative material, comprising: casting the dental polymerizable composition according to claim 5; and then curing the composition through a single heating step.

7. The method for producing a dental restorative material according to claim 6, wherein the dental polymerizable composition is cured through formation of a urethane bond, and radical polymerization of the radical polymerizable group, in the heating step.

8. The method for producing a dental restorative material according to claim 6, wherein the dental polymerizable composition is prepared by mixing a composition (a) containing the polyfunctional isocyanate compound and a composition (b) containing the polyol compound or the polythiol compound, and at least one of the composition (a) and the composition (b) contains an inorganic filler.

* * * * *